United States Patent [19]

Yasuda et al.

[11] 4,260,978
[45] Apr. 7, 1981

[54] GAS DETECTOR ELEMENT

[75] Inventors: Eturo Yasuda; Yoshihiro Segawa, both of Okazaki; Minoru Ohta, Anjo, all of Japan

[73] Assignee: Nippon Soken, Inc., Nishio, Japan

[21] Appl. No.: 40,874

[22] Filed: May 21, 1979

[30] Foreign Application Priority Data

May 19, 1978 [JP] Japan .................................. 53-60530

[51] Int. Cl.³ ............................................. H01L 7/00
[52] U.S. Cl. ..................................... 338/34; 73/27 R; 422/98
[58] Field of Search ...................... 338/34, 229; 73/23, 73/27 R; 324/65 P; 422/98

[56] References Cited

U.S. PATENT DOCUMENTS 3,932,246  1/1976  Stadler et al. ...................... 338/34 X

FOREIGN PATENT DOCUMENTS 1511  4/1979  European Pat. Off. .................. 338/34

Primary Examiner—C. L. Albritton
Attorney, Agent, or Firm—Cushman, Darby & Cushman

[57] ABSTRACT

A gas detector element comprising a sintered material of a metal oxide, the electric resistivity of which varies depending on an oxidative atmosphere or a reductive atmosphere of the inflammable gas composition. said gas detector element being characterized in that the size of the composing particles of said sintered material is in the range from $0.5\mu$ to $5\mu$ in an equivalent circle diameter.

3 Claims, 6 Drawing Figures

10μ

10μ

GAS DETECTOR ELEMENT

The present invention relates to a gas detector element used in a gas detector employed in a feed-back type exhaust gas cleaning system using, for example, a ternary catalyst converter.

Recently, in respect to the exhaust gas cleaning countermeasure of an internal combustion engine, a gas detector is used as a means for detecting an air/fuel ratio of the mixed gas fed for combustion in the internal combustion engine. That is, as a countermeasure for cleaning an exhaust gas of the internal combustion engine, if, for example, a catalyst is used for cleaning an exhaust gas, it is always necessary to maintain the air/fuel ratio of the mixed gas at a suitable value in order that the catalyst performs the maximum function. However, when a fuel feeding apparatus such as carburetor or a fuel jet apparatus of a conventional internal combustion engine is used, the air/fuel ratio of the exhaust gas actually varies largely, though the air/fuel ratio of the mixed gas is set at a fixed value. Consequently, it is required to detect the actual air/fuel ratio of the exhaust gas by any means and to feed back the signal to said carburetor or the fuel jet apparatus in order to keep the air/fuel ratio of the mixed gas at a fixed value. In order to detect the air/fuel ratio by means of a gas detector, the said gas detector must detect directly the air/fuel ratio taking advantage of the close relation of the change of the concentration of each component of the exhaust gas with the air/fuel ratio of the mixed gas.

Heretofore, as one of the methods for detecting the air/fuel ratio of the exhaust gas of an internal combustion engine, there has been a method for detecting the change of the electric resistivity of a metal oxide such as titanium oxide and the like which is responsive to the change of the concentration of the exhaust gas components. The main part of the gas composition detector is composed of a gas detector element comprising a sintered material of a metal oxide showing the electric resistivity which is responsive of the change of the concentration of the gas components in the gas (exhaust gas) to be detected, a pair of electrodes adapted to pick up the electric resistivity connected with said gas detector element, the terminal side of which is embedded or exposed, and a holder comprising a heat-resistant electrically insulating metal oxide for holding a gas detector element by means of said electrodes.

Figure 1:
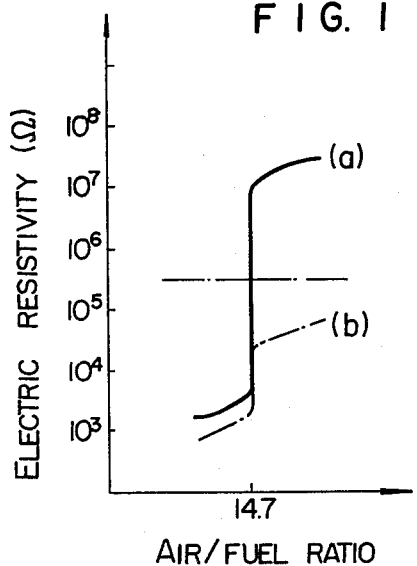
FIG. 1 is a characteristic diagram of the gas detector element of the prior art.

Usually, an internal combustion engine may sometimes be operated for a long period of time under a condition of a high speed and a heavy load and, in such a case, it is necessary to set the air/fuel ratio of the mixed gas at a level lower than the theoretical value of air/fuel ratio (that is to say, to increase the concentration of the fuel component) and hence a gas detector element comprising said titanium oxide is exposed to the high temperature reductive atmosphere of the exhaust gas for an extended period of time. It was found that, when the gas detector element is thus exposed for an extended period of time continuously at the high temperature, to reductive atmosphere of the exhaust gas, the electric resistivity of said element varies largely in an oxidative atmosphere of the exhaust gas and said element does not indicate a true electric resistivity. This is shown in FIG. 1. In FIG. 1, (a) is the characteristic curve of the initial electric resistivity and (b) is the characteristic curve of the electric resistivity after exposure of the element for a long period of time at a high temperature, to reductive atmosphere of the exhaust gas. In FIG. 1, if the one-point dotted line is considered as a set level of the air/fuel ratio, the curve (b) does not cross the set level in the oxidative atmosphere of the exhaust gas and hence, when the air/fuel ratio of the mixed gas in an internal combustion engine is higher than the theoretical value of air/fuel ratio (that is, the concentration of the fuel component is low and the exhaust gas is in the oxidative atmosphere), a signal returning said air/fuel ratio to the theoretical value of air/fuel ratio can not be transmitted to said carburetor or fuel-jet apparatus and therefore it is impossible to keep the air/fuel ratio of the mixed gas at a fixed level.

Consequently, the present inventors have made an extensive research investigation on the cause of great change in the electric resistivity of said element in the oxidative atmosphere and found that, if a gas detector element comprising, for example, titanium oxide is exposed to the reductive atmosphere of the exhaust gas, the composing particles of said gas detector element, that is, titanium oxide particles are reduced to indicate a decreased electric resistivity, and, if said element is exposed to an oxidative atmosphere of the exhaust gas under this condition, the reduced particles are oxidized to indicate an increased electric resistivity, but, if the particles are exposed to the reductive atmosphere of the exhaust gas for a long period of time continuously, the reduced region of the particles is enlarged and a long period of time is required before the reduced region is fully oxidized when the exhaust gas becomes an oxidative atmosphere.

It has been found that, particularly when the size of the composing particles is large, the particles are oxidized only partially and most of the reduced region remains unchanged. Consequently, even after the exhaust gas has been changed to an oxidative atmosphere, the electric resistivity remains at a low level by the influence of a low electric resistivity in the reduced region. On the other hand, if the size of the composing particles of the gas detector element is small, the mean pore size of the gas composition detector element becomes smaller (that is to say, the porosity becomes smaller), and hence the exhaust gas hardly penetrates into the inside of the gas detector element, resulting in the delay of the replacement velocity of the exhaust gas before the change of the gas composition present in the inside of the gas composition detector element even after the change of the gas composition of the exhaust gas. As the result, it was found that the reduced region are remains unoxidized in the inside of the gas composition detector element and the gas detector element indicates a reduced electric resistivity even in an oxidative atmosphere similar to that shown in a reductive atmosphere.

Particle size distribution of the after-milled particles of the element of FIGS. 4 and 5 in the attached drawing is shown in Table 1 as follows:

TABLE 1

Figure 4:
FIG. 4 and FIG. 5 are electronic microscopic photographs showing the surface of the gas composition detector element of the present invention.
Figure 5:
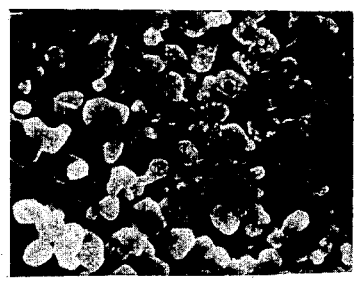

| | After-milled particle size distribution | |
|---|---|---|
| | Particle size distribution (% by weight) | |
| Particle size ($\mu$) | Element of FIG. 4 | Element of FIG. 5 |
| 44 | 100 | 100 |
| 20 | 100 | 100 |
| 10 | 100 | 100 |
| 5 | 85 | 98 |
| 2 | 61 | 87 |
| 0.5 | 28 | 50 |

An object of the present invention is to provide a gas composition detector element, the size of the composing particles of which is set in the range from $0.5\mu$ to $5\mu$, whereby when, after the gas detector element has been exposed for an extended period of time continuously to a reductive atmosphere of the exhaust gas, the exhaust gas is converted into an oxidative atmosphere, the reduced region in the inside of the gas detector element formed in the reductive atmosphere is instantly oxidized to indicate an electric resistivity corresponding to the oxidative atmosphere, causing no great change in the electric resistivity in an oxidative atmosphere.

The present invention is illustrated by way of a concrete example hereinbelow.

EXAMPLE 250 g of the titanium oxide powder stabilized by calcinating at 1200° C. was pulverized in a ball mill (capacity 1 l). Subsequently, 1 part of 6% (w/w) aqueous solution of polyvinyl alcohol (having degree of polymerization is 500) was added as an organic binder to 6 parts of the powder to prepare granules having diameter of 50–200$\mu$. The granules were placed together with platinum electrodes in a mold and subjected to pressure-molding under the pressure of 1,000 Kg/cm² for 3 seconds and then the molding was sintered at 1100° C. for 2 hours. Thereafter, the sintered material was immersed for an hour at a room temperature in 1 l of an aqueous solution of chloroplatinic acid (prepared by dissolving 100 g of chloroplatinic acid in water to make 1 l of the solution) and then dried and sintered at about 800° C. for 2 hours to obtain a gas detector element.

Figure 2:
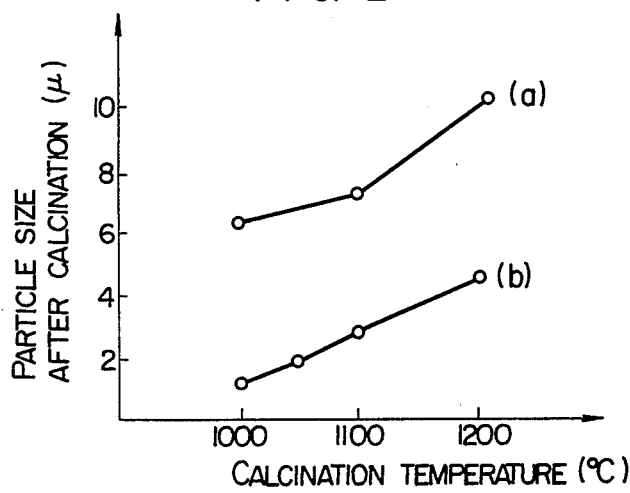
FIG. 2 and FIG. 3 are characteristic diagrams of the gas composition detector element of the present invention.

Several gas detector elements thus prepared having different sizes of the titanium oxide particles were provided. It is easy to change the size of the composing particles from the relation between the particle size of the raw material (titanium oxide) after said calcination, sintering temperature and the particle size after sintering as shown in FIG. 2. In FIG. 2, (a) shows the characteristic property when the particle size of the raw material is $5\mu$ and (b) shows the characteristic property when the particle size is $0.7\mu$. The size of the particles of the raw material after calcination and that of the particle size after sintering was measured according to the well known Heywood method using the electronic microscopic photograph. The particle size was calculated by the following equivalent circle diameter according to the Heywood method.

Equivalent circle diameter $D = \sqrt{4f/p}$ wherein D is a particle size and f is an area of the particle. The gas detector elements thus prepared having different particle sizes were placed in an exhaust tube of an automobile engine and said gas detector elements were exposed for 10 to 100 hours continuously to the reductive atmosphere of the exhaust gas at a high temperature of 800° C. at the air/fuel ratio of 12.2 in the exhaust gas side. Thereafter, the electric resistivity of the gas detector element was measured in an oxidative atmosphere of the exhaust gas at a low temperature of 500° C. at the air/fuel ratio of 16.1 in the exhaust gas side after each durable time. On the other hand, the electric resistivity of said gas detector element without undergoing said continuous durable test was measured in said oxidative atmosphere and the change in the electric resistivity before and after the durable test was observed. The results were shown in FIG. 3.

Figure 3:
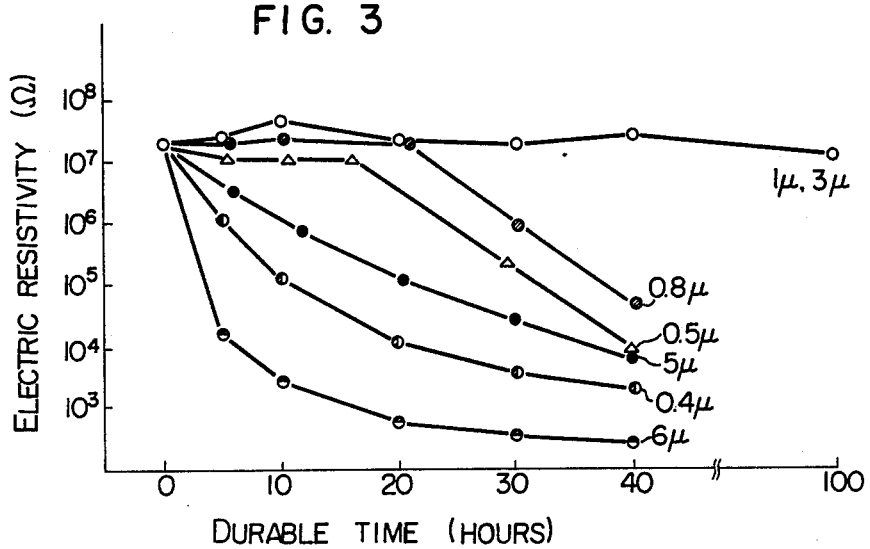

In FIG. 3 the figures appeared at the end of each curves mean typical particle size ($\mu$) which relate to the maximum value in the respective particle size distribution as shown in Table 2 below.

TABL 2

| | Particle size distribution (% by weight) | | | | |
|---|---|---|---|---|---|
| Particle size ($\mu$) | Typical particle size | | | Element of FIG. 4 | Element of FIG. 5 |
| | 3 $\mu$ | 5 $\mu$ | 6 $\mu$ | | |
| 9 | 100 | 100 | 100 | 100 | 100 |
| 8 | 100 | 100 | 100 | 96 | 100 |
| 7 | 100 | 100 | 100 | 92 | 100 |
| 6 | 100 | 100 | 100 | 76 | 100 |
| 5 | 100 | 100 | 90 | 60 | 100 |
| 4 | 100 | 92 | 82 | 40 | 100 |
| 3 | 100 | 80 | 40 | 24 | 89 |
| 2 | 60 | 20 | 10 | 10 | 26 |
| 1 | 20 | 10 | 5 | 3 | 10 |

As can be seen from said FIG. 3, the gas detector elements having the particle size of $1\mu$, $3\mu$ and $5\mu$ in equivalent circle diameter showed almost the same resistivity as the initial value even after the test of 100 hours, there being almost no change in the electric resistivity. In contrast, it was found that the electric resistivity of the gas detector element having the particle size of $0.5\mu$ and $0.8\mu$ in equivalent circle diameter changed sharply after the test exceeding about 15 to 20 hours. On the other hand, it was found that the electric resistivity of the gas detector element having the particle size of $0.4\mu$ and $6\mu$ in equivalent circle diameter changed sharply after the test exceeding 2 to 3 hours. During driving of an automobile on a high-way, the internal combustion engine is operated under a condition of a high speed and a heavy load for a long period of time and the air/fuel ratio of the mixed gas is naturally reduced (and the concentration of the fuel component is increased) and hence the atmosphere of the exhaust gas becomes reductive. It is experienced frequently that such condition exceeds 2 to 3 hours continuously. Therefore, it is understandable that the gas detector element, the electric resistivity of which in the oxidative atmosphere after exposure to the reductive atmosphere only 2 to 3 hours changes sharply as compared with the initial resistivity value is not practical.

Based on the results in FIG. 3, the present inventors have made further studies and found that the desirable size of the composing particles of the gas detector element is in the range from $0.5\mu$ to $5\mu$ in corresponding circle diameter and that the most desirable particle size is in the range from $1\mu$ to $5\mu$. An electronic microscopic photograph of the surface of a gas detector element comprising particles having the particle size exceeding 5µ is shown in FIG. 4 and that of a gas detector element comprising particles having the particle size of about 2 to 3µ is shown in FIG. 5, respectively.

Figure 6:
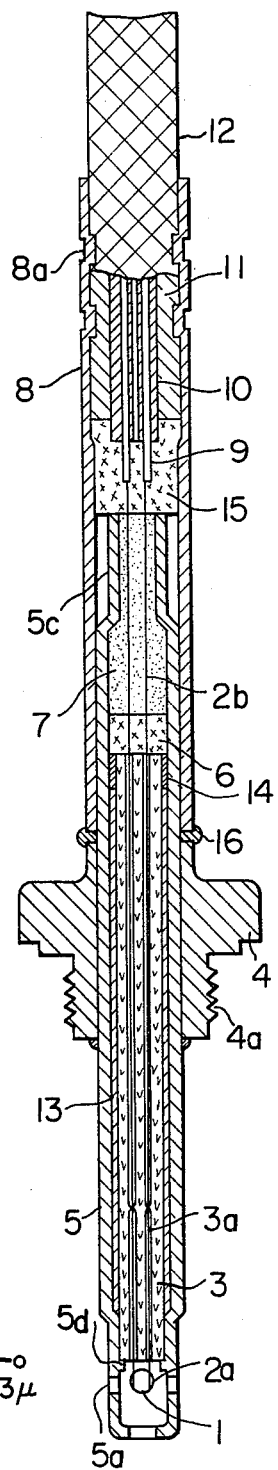
FIG. 6 is a cross-sectional diagram showing the entire structure of the gas composition detector using the gas composition detector element of the present invention.

Subsequently, the entire structure of a gas composition detector using the gas detector element of the present invention is shown in FIG. 6. In FIG. 6, 1 is a gas detector element comprising a sintered material of a metal oxide such as titanium oxide, 2a is a pair of electrodes comprising platinum or the like embedded in the gas detector element 1, 2b is a pair of sublead wires comprising a heat resistant metal such as stainless steel and the like electrically connected by welding with the electrodes 2a, 3 is a cylindrical ceramic body having a pair of narrow penetrating pores 3a of the same diameter, into which said electrodes 2a and sub-lead wires 2b are inserted, respectively. Said cylindrical ceramic body is composed of a heat resistant electrically insulating ceramic such as alumina or the like. 4 is a housing comprising a heat-resistant metal having a screw portion 4a for fixing it on the exhaust tube, 5 is a pipe comprising a heat-resistant metal having plural pores 5a for the passage of the exhaust gas, on the bottom side of which is formed a projection 5d of a ring form, and the ceramic body 3 is held on said projection 5d, 6 is a glass seal material in a solid state, which is packed to fill up the opening of the penetrating pores 3a of the ceramic body 3 between the ceramic body 3 and the pipe 5. Seal of the exhaust gas and insulation and fixation of the sub-lead wires 2b is secured by this glass seal material 6. 7 is a powder such as alumina-magnesia or the like and keeps the fixative electric insulation between the sub-lead wires 2b, 9 is a pair of lead wires connected by welding with said sub-lead wires 2b. A cover 10 comprising a heat resistant and electrically insulating material such as glass wool or heat resistant rubber or the like is put on the outside of the lead-wires 9. Furthermore, another cover 11 of the same material is put on said cover 10 and both lead wires 9 are electrically insulated each other. 12 is a cover made by knitting the heat resistant metal and is put on said cover 11. Said cover 12 is fixed on the pipe 8 by pushing the end portion of the pipe 8 into the inside as shwon by 8a. The end portion of the pipe 5 is pushed in as shown by 5c to increase the pack density of the electrically insulating powder 7 of the inside 13 is an inorganic adhesive such and is injected into the gas between the ceramic body 3 and the pipe 5 and solidified. The ceramic body 3 and the pipe 5 are fixed strongly by this adhesive 13. 14 is a heat-resistant metal ring for compressing the adhesive 13. 15 is a heat-resistant rubber such as silicone rubber and the like arranged between the pipe 5 and the outmost cover 12 of the lead wire 9 in the pipe 8. Pipe 8 and housing 4 are fixed by welding at the site of signal 16.

The present invention is not limited to above-said example and can be modified variously as shown hereinbelow.

(1) The gas composition detector element of the present invention is characterized in the size of the composing particles and is not limited to the material of, titanium oxide. It may be composed of zinc oxide, nickel oxide, stannic oxide, niobium oxide and the like.

(2) The present invention can be applied to the usages other than the exhaust gas cleaning system.

As mentioned above, according to the present invention, the size of the composing particles of the gas detector element is set in the range from $0.5\mu$ to $5\mu$ and when this gas detector element is exposed to the reductive atmosphere of the inflammable gas for an extended period of time continuously and then the component of the atmosphere is converted into an oxidative one, the reduced region in the gas detector element formed in the reductive atmosphere is instantly oxidized, leaving no reduced region unlike the conventional gas detector element. Thus, there is obtained an electric resistivity corresponding to an oxidative atmosphere. Therefore, according to the present invention, the conventional defect that, after the gas detector element has been exposed to a reductive atmosphere for an extended period of time continuously, the electric resistivity of the gas detector element changes markedly if the reductive atmosphere is converted into an oxidative one is dissolved and consequently there is an effect that an inflammable gas atmosphere can be detected correctly.

What is claimed is:

1. In a gas detector element comprising a sintered material of a metal oxide, the electric resistivity of which varies depending on whether the composition of the inflammable gas is an oxidative atmosphere or a reductive atmosphere, the size of the composing particles of said sintered material is in the range from $0.5\mu$ to $5\mu$ in equivalent circle diameter.

2. A gas detector element according to claim 1, wherein the size of the composing particles of the sintered material is in the range from $1\mu$ to $5\mu$ in corresponding circle diameter.

3. A gas detector element according to claim 1 or 2, wherein the material of said sintered material is selected from a group consisting of titanium oxide, zinc oxide, nickel oxide, stannic oxide and niobium oxide.

* * * * *